United States Patent
Zalevsky et al.

(10) Patent No.: US 11,085,753 B2
(45) Date of Patent: Aug. 10, 2021

(54) SYSTEM AND METHOD FOR USE IN REMOTE SENSING

(71) Applicant: CONTINUSE BIOMETRICS LTD., Tel Aviv (IL)

(72) Inventors: Zeev Zalevsky, Rosh HaAyin (IL); Haim Goldenfeld, Rishon Le Zion (IL)

(73) Assignee: CONTINUSE BIOMETRICS LTD., Tel Aviv (IL)

( * ) Notice: Subject to any disclaimer, the term of this patent is extended or adjusted under 35 U.S.C. 154(b) by 27 days.

(21) Appl. No.: 16/484,910

(22) PCT Filed: Feb. 15, 2018

(86) PCT No.: PCT/IL2018/050176
§ 371 (c)(1),
(2) Date: Aug. 9, 2019

(87) PCT Pub. No.: WO2018/150427
PCT Pub. Date: Aug. 23, 2018

(65) Prior Publication Data
US 2020/0072597 A1 Mar. 5, 2020

Related U.S. Application Data

(60) Provisional application No. 62/459,236, filed on Feb. 15, 2017.

(51) Int. Cl.
*G01B 9/02* (2006.01)
*A61B 5/00* (2006.01)
*A61B 5/024* (2006.01)

(52) U.S. Cl.
CPC ........ *G01B 9/02094* (2013.01); *A61B 5/0066* (2013.01); *A61B 5/024* (2013.01)

(58) Field of Classification Search
CPC ..... G01B 9/02094; A61B 5/006; A61B 5/024; A61B 5/021; A61B 5/0816;
(Continued)

(56) References Cited

U.S. PATENT DOCUMENTS

| 6,552,809 | B1 * | 4/2003 | Bergeron ................. G01D 5/38 356/601 |
| 8,638,991 | B2 | 1/2014 | Zalevsky et al. |

(Continued)

FOREIGN PATENT DOCUMENTS

WO 2007142960 A2 12/2007

OTHER PUBLICATIONS

Horch, Elliot P., The Status of Speckle Imaging in Binary Star Research, RevMexAA, 2006, pp. 79-82, vol. 25.

*Primary Examiner* — Mohamed K Amara
(74) *Attorney, Agent, or Firm* — Browdy and Neimark, P.L.L.C.

(57) ABSTRACT

A system for use in monitoring parameters of an object includes an illumination unit configured for providing coherent illumination of a predetermined wavelength range and for directing the coherent illumination onto an inspection region of the object, and a collection unit comprising a lens arrangement and a detector array and configured for collecting light returning from the inspection region and for generating one or more image data pieces associated with speckle patterns generated at an intermediate plane between the inspection region and the detector array. The detector array is configured as a rolling shutter type detector unit and the collection unit comprises at least one light splitting element configured for splitting collected light to thereby form a plurality of image replications corresponding to the speckle patterns on the detector array.

11 Claims, 2 Drawing Sheets

(58) Field of Classification Search
CPC . A61B 5/14532; A61B 5/1455; A61B 5/0059; G01N 2021/479
See application file for complete search history.

(56) References Cited

U.S. PATENT DOCUMENTS

| | | |
|---|---|---|
| 9,636,041 B2 | 5/2017 | Zalevsky et al. |
| 9,668,672 B2 | 6/2017 | Zalevsky et al. |
| 2009/0118623 A1* | 5/2009 | Serov .................. A61B 5/0059 600/476 |
| 2009/0310118 A1 | 12/2009 | Halldorsson |
| 2012/0081566 A1* | 4/2012 | Cote ..................... H04N 5/225 348/222.1 |
| 2014/0036272 A1 | 2/2014 | Nadkarni |
| 2015/0323311 A1* | 11/2015 | Muijs .................. A61B 5/0059 356/28.5 |
| 2016/0327779 A1* | 11/2016 | Hillman ................ G02B 23/04 |
| 2017/0097515 A1* | 4/2017 | Bell ...................... G02B 27/46 |
| 2019/0008388 A1* | 1/2019 | Ando ..................... G01J 3/0208 |
| 2019/0099089 A1* | 4/2019 | Kuwayama ............ G02B 27/48 |
| 2019/0293554 A1* | 9/2019 | Nakao ..................... G01N 21/17 |
| 2019/0355545 A1* | 11/2019 | Zeidler .................. H01J 37/05 |

\* cited by examiner

SYSTEM AND METHOD FOR USE IN REMOTE SENSING

TECHNOLOGICAL FIELD

The present invention is in the field of optical remote sensing and is relevant for monitoring parameters of a sample or patient, e.g. biomedical parameters, while enabling to overcome frame rate limitations of a camera.

BACKGROUND

Various techniques are known, providing non-invasive detection and monitoring of parameters of biological tissues, and generally various other samples. Several such techniques utilize detection of variation in interference pattern from by light components of coherent illumination returning or scattering from the sample to be monitored. Such interference of light components from speckle patterns that can be collected by a defocused imaging system such as camera unit. Generally, temporal variations in the speckle patterns are indicative of variations if the surface from which the light is reflected/scattered. Speckle-based monitoring techniques generally monitor such variations in speckle patterns and determine data about the inspected sample accordingly.

U.S. Pat. No. 8,638,991 presents a method for imaging an object. The method comprises imaging a coherent speckle pattern propagating from an object, using an imaging system being focused on a plane displaced from the object.

U.S. Pat. Nos. 9,668,672 and 9,636,041 present a system and method for use in monitoring one or more conditions of a subject's body. The system includes a control unit which includes an input port for receiving image data, a memory utility, and a processor utility. The image data is indicative of data measured by a pixel detector array and is in the form of a sequence of speckle patterns generated by a portion of the subject's body in response to illumination thereof by coherent light according to a certain sampling time pattern. The memory utility stores one or more predetermined models, the model comprising data indicative of a relation between one or more measurable parameters and one or more conditions of the subject's body. The processor utility is configured and operable for processing the image data to determine one or more corresponding body conditions; and generating output data indicative of the corresponding body conditions.

GENERAL DESCRIPTION

Speckle-based monitoring techniques provides non-invasive and non-contact optical monitoring, enabling detection of various parameters of objects, or biological tissues. Such parameters vary from elastic response, to detection of vibrations associated with biological and biomechanical activity. The main concepts of speckle-based monitoring are generally described in more details in the above mentioned publication. Specifically, the technique may be based on illumination of an inspection region with coherent, or partially coherent illumination, and collecting light reflected/scattered from the inspection region, using defocused camera unit. The so-collected image data pieces include secondary speckle patterns associated with interferences of light components. The technique generally further includes determining one or more correlation functions (e.g. spatial correlation) between speckle patterns in one or more sequences of collected images. Variation of the correlation between consecutively collected speckle patterns is indicative of change in orientation, curvature and/or location of surface at the inspection region. Such monitoring techniques enables detection of various parameters including for example acoustic signals, heart rate, breathing rate, pulse velocity, blood pressure etc. Additional parameters such as elastic response, glucose blood concentration and alcohol concentration in blood, may require additional external stimulation to magnify desired signals associated with the parameter to be measured.

Generally, to properly extract accurate and relevant signal data about a sample, e.g. living biological tissue, frame rate of the collected image data (rate of speckle pattern collection) is required to at least satisfy Nyquist condition. For example, to properly determine data indicative of parameters such as heart activity (e.g. heart rate with typically periodicity of 40-200 bpm), and respiratory activity of a patient, the frame rate for collection of speckle patterns may often be around 300-400 fps and higher. This is while suitable camera units are relatively expensive.

On the other hand, conventional camera units, e.g. handheld camera such as smart phone camera, are typically capable of sampling at relatively lower frame rate of 30 fps, and at times with a frame rate of 60 fps. This is while conventional hand-held camera units (e.g. smartphones) can provide relatively high spatial resolution raging above 1000×1000 pixels and at times reaching resolution of 4 Mpixel, 16 Mpixels and even 32 Mpixels.

The inventors of the present invention have found that a use of spatial-temporal tracking of the secondary speckle patterns generated by light returning from an inspection region of a sample may enable accurate monitoring of various parameter while utilizing relatively low frame rate detection. The present technique utilizes one or more light splitting elements configured for providing two or more copies of collected speckle patterns on a rolling shutter type detector array. This technique utilizes readout scheme of the detector array to provide time variation between readings of the different copies, thus forming corresponding plurality of speckle pattern data collected at different times, within exposure time of a single image.

To this end the present invention provides a system and method for use in monitoring of a sample. The system comprises an illumination unit configured for providing coherent illumination of one or more predetermined wavelength ranges and for directing said coherent illumination onto one or more inspection regions of the object, and a collection unit comprising at least one detector array and at least one corresponding imaging lens arrangement and configured for collecting light returning from the inspection region and generate one or more image data pieces associated with speckle patterns generated by interference of light components returning from the sample, e.g. at an intermediate plane between the inspection region and said detector array.

Generally, the detector array is configured as a conventional detector array, which may have relatively low frame rate, and utilizing a moving/rolling shutter configuration. The collection unit further comprises at least one light splitting element (e.g. diffractive element) configured for splitting collected light to form a plurality of image replications corresponding to a collected speckle patterns on the detector array. It should be noted that such light splitting element may generally be a diffractive element such as grating, a collection of beam splitters or have other configurations. For simplicity the light splitting elements is described herein below as diffractive element, however it should be understood that additional light splitting elements and/or configurations may be used. It should also be noted that the use of coherent illumination, typically having well defined and narrow wavelength range (e.g. provided by a continuous wave laser unit), enables selection of a diffractive element to be optimized for a specific wavelength provided by the illumination unit. However, as indicated above, various other optical elements may be used providing light splitting to form plurality of image replications using reflective, refractive and diffractive features of light.

The light splitting (e.g. diffractive) optical elements is typically positioned in the collection unit in optical path of light collected from the inspection region. The optical element is configured to direct the collected light to form a plurality of image replications, e.g. associated with diffraction lobes, of the collected light. This plurality of image replications is directed to the detector array to form a plurality of replications of images region, each including speckle pattern corresponding to light interferences along path of light propagation from the inspection region.

The present technique utilizes the rolling shutter operation of the detector array for providing high sampling rate that exceeds nominal sampling rate of the detector array. The arrangement of the different replica of the collected images is selected to provide temporal difference in collection of the image data. The temporal difference between image data portions associated with different replications of the speckle pattern is generally determined in accordance with rolling shutter operation scheme.

To this end, the system may also comprise, or be connectable to, a control unit. The control unit generally comprises a processing utility comprising one or more processors, and a storage utility. The control unit is configured and operable for receiving input data comprising one or more sequences of image data pieces, generally at the frame rate of the camera unit (of its detector array). Each of the image data pieces typically corresponds to an image collected by the detector array and a certain time (in accordance with the rolling shutter readout technique), and includes a plurality of image portions associated with different image replications of collected speckle patterns. It should be noted that due to the rolling shutter configuration of the detector array, the different image replications correspond to slightly different acquisition times in accordance with operation speed of the rolling shutter.

Thus, end the control unit may comprise pre-stored data about operation time of the rolling shutter, or be configured for extracting such data from the received image data pieces. The control unit is thus configured and operable for extracting the different image replications from the received image data pieces, and for processing received plurality of images associated with secondary speckle patterns generated by light returning from the inspection regions and collected at a sequence of acquisition times.

The control unit is may generally be further configured and operable for processing data indicative of the plurality of so-collected images and determine correlation function between speckle patterns collected in consecutive images. Such correlation is indicative of variations (e.g. vibrations) of the surface at the inspection region, which in turn may provide data indicative of various parameters of a sample/tissue being monitored. Such parameters may include elastic/plastic response to external stimulation, heart rate and heart performance of a patient, respiratory operation, blood related parameters (such as glucose or alcohol content), etc.

Thus according to a broad aspect thereof, the present invention provides a system for use in monitoring parameters of an object, the system comprising an illumination unit configured for providing coherent illumination of a predetermined wavelength range and for directing said coherent illumination onto an inspection region of the object, and a collection unit comprising a lens arrangement and a detector array and configured for collecting light returning from the inspection region and for generating one or more image data pieces associated with speckle patterns generated at an intermediate plane between the inspection region and said detector array; wherein said detector array is configured as a rolling shutter type detector unit and said collection unit comprises at least one light splitting element configured for splitting collected light to thereby form a plurality of image replications corresponding to said speckle patterns on said detector array.

According to some embodiments, the plurality of image replications may be formed on different regions of the detector array. Generally the readout of the plurality of image replications provides time shift in collection between different replications thereby enhancing collection frame rate of the system.

According to some embodiments, the system may further comprise a control unit connectable to the collection unit and configured and operable for receiving and processing said one or more image data piece for determining one or more parameters of the object; the control unit is configured for utilizing data about operation of the rolling shutter type detector unit and for extracting, from each image data piece, said plurality of image replications corresponding to collected speckle patterns, and for processing the so extracted images to determine correlation between consecutive speckle patterns indicative of said one or more parameters. Generally the control unit may be configured as a computer unit comprising one or more processors a storage utility. The control unit may further be pre-loaded with computer readable instructions that, when executed by a processor, caused the processor to operate the system including illumination and collection unit, and to be responsive to image data pieces received from the collection unit to thereby enable processing of the image data in accordance with pre-stored data on rolling shutter operation of the detector unit. Typically the control unit is configured to determine one or more parameters of the sample based on the determined correlation between speckle patterns along selected monitoring time.

Generally the light splitting element may be a diffractive optical element. Alternatively, the light splitting element may be configured for splitting collected light using refractive or reflective properties.

According to some embodiments, each image data piece generated by the detector array may correspond to a number of image regions collected at different timing, thereby increasing sampling rate of the system by a factor on the range between 4 and 20.

The lens arrangement of the collection unit may be configured to provide defocused image of the inspection region on the detector array to thereby increase contract of the collected speckle patterns.

Generally, according to some embodiments, the at least one light splitting element is located along optical path between said lens arrangement and the detector array.

It should be noted that the rolling shutter type detector unit may comprise a digital detector array configured for row-by-row digital readout operation. However, in some other configurations, the rolling shutter type detector unit may comprise a digital detector array configured for simultaneous readout and a moving slit providing rolling shutter exposure operation.

According to yet another broad aspect of the invention, the present invention provides a detection unit comprising optical arrangement and a detector array operable as rolling shutter detector having certain frame rate, said optical arrangement comprises one or more light splitting elements and is configured for collecting light arriving from a scene and for generating a plurality of image replication associated with light pattern collected from the scene, and for projecting said plurality of image replications on the detector array, thereby enabling said detector unit to collect image date at sampling rate that exceeds said certain frame rate of the detector array by a factor of number of the replications. Configuration and operation techniques, as well as association of the detector unit with a corresponding control unit are as described herein.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
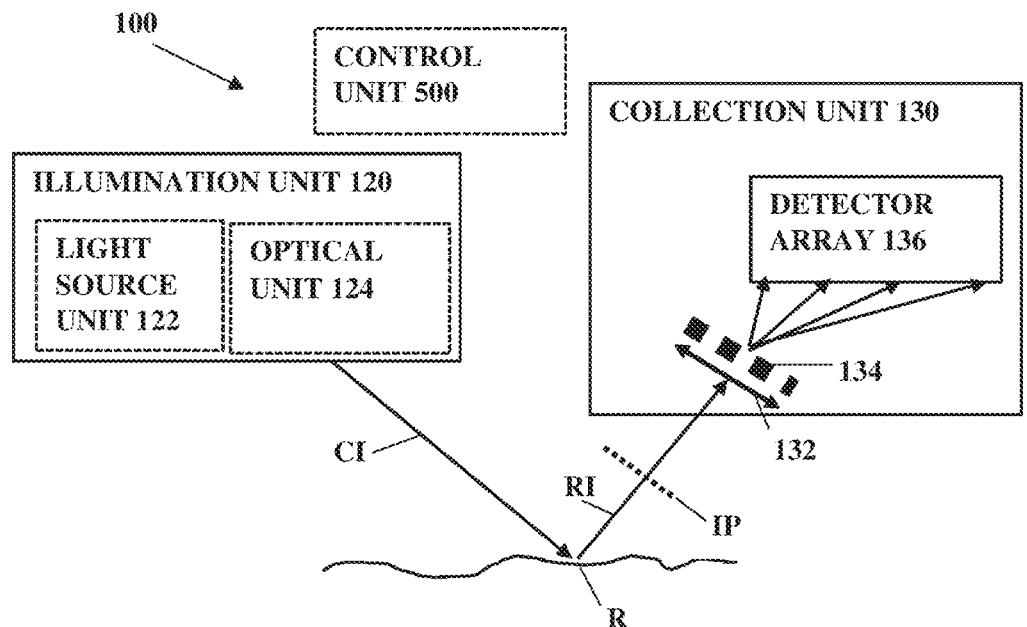
FIG. 1 illustrates schematically a system for monitoring a sample according to some embodiments of the invention.

Reference is made to FIG. 1 illustrating schematically a system 100 for remote sensing and monitoring of an object. The system 100 is generally configured for monitoring one or more selected inspection regions R of the object/sample. The sample may generally be of any type including for example, rocks, artificial structures, wood, plastic, biological tissue, patient body etc. Preferably, the present technique may be used for monitoring biomedical parameters of a person, and accordingly the sample and the inspection region R may be associated with one or more body parts of the person, directly on the skin or over clothes.

The system 100 is generally configured for optical monitoring of the inspection region R using speckle based technique, while enabling accurate detection utilizing detector array having relatively low frame rate. The system includes an illumination unit 120 and collection unit 130, and may typically include, or be connectable to, a control unit 500 configured for operating the illumination and collection units and for receiving and processing collected image data pieces from the collection unit for monitoring the inspection region R.

As indicated, system 100 includes an illumination unit 120 in configured for providing coherent illumination CI and for directing the coherent illumination CI onto one or more inspection regions R of the sample (e.g. body region of a patient), and a collection unit 130 configured for collecting light RI returning from the inspection region(s) R and for generating a sequence of image data pieces associated with secondary speckle pattern formed by light interferences at an intermediate plane IP located between the inspection region R and the collection unit 130 or further than the inspection region R.

The illumination unit 120 may typically include at least one light source unit 122 and may include at least one corresponding optical unit 124. The light source unit 120 may be a laser unit or any other type of light source capable of providing coherent optical illumination at a selected wavelength range. The optical unit 124 may be used for directing the coherent illumination onto the inspection region R. The optical unit 124 may generally include one or more lenses, mirrors or any other optical element for directing illumination and form one or more illuminated spots of desired dimension at selected locations for inspection.

The collection unit 130 includes a detector array 136, configured as a rolling shutter detector array, an imaging lens unit 132 and a light splitting optical element 134. The light splitting optical element 134 may generally be a diffractive optical element such as grating and is referred to as such herein below, however, it should be noted that in some embodiments the light splitting optical element may utilize refractive, reflective features and/or a combination thereof. The lens unit 132 is configured, by location with respect to the detector array 134 and optical power of the lens unit, to provide defocused imaging of the inspection region R. This configuration enables collection of image data associated with secondary speckle pattern (formed by interference of light components scattered/returned from the inspection region R) while reduces signal associated with focused image of the inspection region. The lens unit may be configured for directing collected light such that an image formed on the plane of the detector array 136, corresponds to an intermediate plane IP located between the inspection region R and the lens unit 132, or associated with a plane that is distant with respect to the inspection region R.

Additionally, according to the technique of the present invention, the collection unit includes a light splitting element 134 located in optical path between the lens unit 132 and the detector array 136. Generally, the light splitting (e.g. diffractive) optical element 134 may be located directly on (e.g. at an exit pupil) the lens unit 132. However configurations may be used where the light splitting element 134 is located a short distance downstream of the lens unit 132. The light splitting element 134 may for example be configured as diffractive grating, or any other diffractive element, configured for directing light into several diffraction orders. The lens unit 132, diffractive element 134 and detector array 136 are arranged such that light collected by the lens unit 132 is diffracted by the diffractive element 134 to form a plurality of predetermined number of image replications on the detector array 136 as exemplified in FIG. 2.

It should be noted that generally the lens unit 132 may be configured for forming and image onto a small portion of the detector array 136, this may be provided using one or more field apertures limiting light collection by the lens unit 132 and corresponding light transmission toward the detector array 136. Thus a single image replication is projected on the detector array 136 taking only a small portion of the array surface, and additional image replications may be projected on the detector array with limited, and preferably no, overlapping between them.

Figure 2:
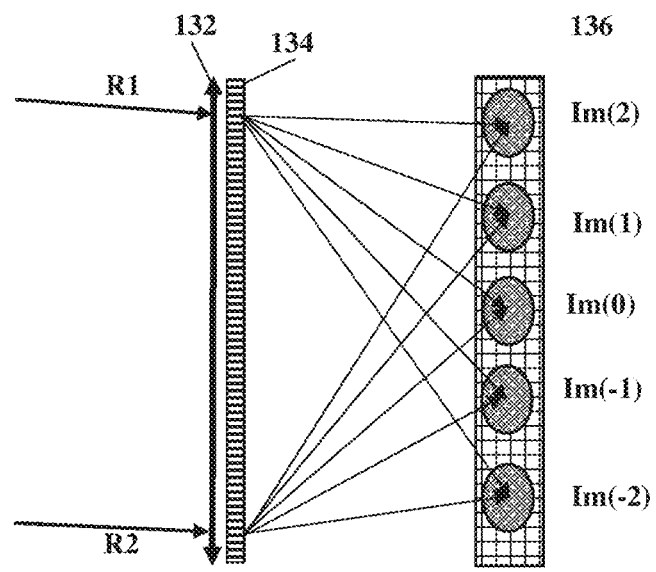
FIG. 2 illustrates path of light collection using a diffractive optical element according to some embodiments of the invention.

FIG. 2 illustrates schematically path of light collected by the lens unit 132 of the collection unit 130, and transmitted to form plurality of image replications on the detector array 136. As shows, light collected from the inspection region R is transmitted and refracted by the lens unit 132 to form defocused image including one or more speckle patterns. The light is further diffracted by the diffractive optical element 134 to a plurality of diffraction orders, thereby forming a plurality of image replications on the detector array 136. FIG. 2 exemplifies light collection illustrating two peripheral light rays R1 and R2 and diffraction of light passing through the diffractive optical element 134 to form a plurality of image replications on the detector array 136. Five such replication Im(2), Im(1), Im(0), Im(−1) and Im(−2) are exemplified in FIG. 2. According to some embodiments, the diffractive element 134 may be located at an exits aperture of the lens unit 132, alternatively, the diffractive element 134 may be located on an image plane with respect to the lens unit 132. Alternatively, the diffractive element may be located at an intermediate plane, where the detector array 136 is located at the respective image plane (corresponding to intermediate object plane (IP in FIG. 1).

Figure 3:
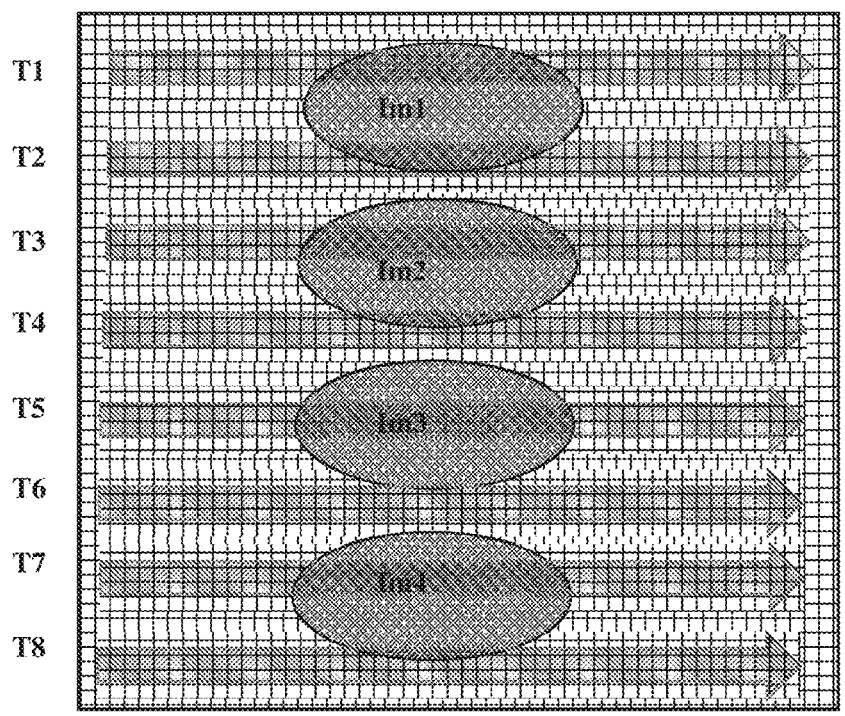
FIG. 3 exemplifies image replications formed on the detector array and temporal delay in collection of the replications using rolling shutter detector according to some embodiments of the invention.

As indicated above, the technique of the present invention utilizes the typical operation scheme of rolling shutter detector arrays 136. The use of the rolling shutter operation in combination with the technique of the invention is exemplified in FIG. 3, illustrating several image replications Im1-Im4 formed on surface of a detector array 136. In this example, four image replications are exemplified, numbered Im1-Im4, to simplify understanding. However, various other numbers of image replications may be used, providing a factor of increasing effective sampling rate as described herein below.

Generally, rolling shutter operation comes from analog detection techniques, where an actual shutter having a slit is moved in front of a film to allow light to reach the active material of the film. The slit is moved along the film region such that at any given moment only a region of the film is exposed, such that the entire region of the film is exposed for a selected duration, with time differences between regions. It should be noted that the detector array 136 may be configured to provide digital row-by-row readout. Alternatively, the detector array 136 may be configured as digital detector array providing simultaneous/parallel readout of pixels/rows of the array. In these configurations, the collection unit may further include a mechanic moving window or slit that provides rolling shutter operation by affecting the exposure of the detector array to input light. In some additional configurations, the rolling shutter may be provided by a spatial light modulator located upstream of the detector array and provides row by row, or region by region exposure of the detector array pixel elements. This configuration also enables two-dimensional light splitting element 134 forming a two-dimensional array of image replications on the detector array.

The case of digital detector array is somewhat different, but has similar effect as the analog technique. The detector array is formed by rows of detection elements such as photodiodes, where each detector element can be operated for light collection, undergo readout, and get prepared for an additional cycle of light collection. In some configurations, each photodiode is coupled to a capacitor, where the capacitor may be discharged to prepare for exposure time, charged by electric charges from the photodiode in response to exposure to light, and then the charge level of the capacitor is measured and collected for readout. In a typical detector array, the operation cycle of the detector elements is serial, and performed row by row of detector elements. This results in time variations between readout time of the top row elements, e.g. row T1, and the bottom row elements, e.g. row T8. As a result, image replication Im1 is collected, for generating portion of the image data, some time prior to collection of image replications Im2 and further prior to collection of image portions Im3 and Im4, all within the time required for collection of image data of a single frame. Thus, a single image data piece, associated with readout of the entire array of the detector array 136, includes several image replications of speckle patterns, formed and collected at different times in accordance with operation speed of the detector array, effectively multiplying collection frame rate by the number of image replications on the detector array 136.

As indicated above, the collection unit (130 in FIG. 1) is configured for generating a sequence of image data pieces. The present technique utilizes the use of the diffractive element 134 and the rolling shutter operation of the detector array 136, to provide that each image data piece actually includes certain predetermined number of images taken in different times. The collection unit 130 is further configured for transmitting the collected sequence of image data pieces for processing. Generally, as indicated above, the system may include a control unit 500, configured for receiving the sequence of image data pieces and for processing and analyzing variations in speckle patterns as collected over time.

Referring back to FIG. 1, the control unit 500 may typically include a processing utility, e.g. including one or more processors, and may also include a storage utility and input and output communication ports. Generally, the storage utility may be used for storing data indicative of operation scheme of the detector array 136, such as operation speed of the rolling shutter thereof, and may also be used for storing data about the received imaged data pieces, intermediate processing data and processing intermediate results and output. The processing utility is configured and operable for receiving the image data pieces, processing each image data piece utilizing data about operation of the rolling shutter, for extracting data about the plurality of different image replications (such as Im1-Im4) and corresponding time tags indicative of acquisition time thereof. The processing utility is generally further configured for processing data about the different images for determining correlation functions between consecutively collected speckle patterns. Such correlation between speckle patterns may be further processed for determining various parameters of the sample/tissue as mentioned above.

Thus, the technique of the present invention utilizes rolling shutter operation of a typical detector array, e.g. as provided in various types of camera units, in combination with the relatively high image resolution (geometrical resolution of the detector array) to compensate the relatively low frame rate of typical camera and enable high temporal resolution and sampling rate of data collection. Generally, as the diffractive element 134 projects higher number of image replications on the detector array 136, the higher the temporal resolution of monitoring using the collected images. For example, using a detector array operating at frame rate of 30 frames per second, and a diffractive element providing 5 image replications on the detector array. The total image acquisition rate of speckle patterns will be 30 fps times 5 replications per frame provides 150 patterns per second. If the light splitting (diffractive) element 134 is configured and located such that it generates 10 image replications on the detector array 136, the total image acquisition rate is 30×10=300 patterns per second. Generally, the light splitting element 134 may be configured to generate 15 image replication providing total image acquisition rate of 30×15=450 patterns per second.

The present technique is thus based on suitably splitting collected light (by diffractive element or other optical splitter elements) into a plurality of image replications having a predetermined arrangement on the detector array. The detector array utilizes rolling shutter operation scheme providing that different portions of the frame (e.g. rows) are read with temporal difference between them, providing variation in acquisition time for the different image replications. Utilizing data about operation of the rolling shutter, the image replications may be arranged by chronologic order and processed and analyzed to determine high temporal resolution data about the sample being monitored.

The invention claimed is:

1. A system for use in monitoring parameters of an object, the system comprising an illuminator configured to produce coherent illumination of a predetermined wavelength range and direct said coherent illumination onto an inspection region of the object; and a collection unit comprising a lens arrangement and a detector array and configured to collect light returning from the inspection region in response to said illumination and to generate one or more image data pieces associated with speckle patterns generated at an intermediate plane between the inspection region and said detector array; wherein said detector array is configured as a rolling shutter type detector unit; and said collection unit comprises at least one light splitter configured to split the light being collected to thereby form simultaneously a plurality of image replications corresponding to said speckle patterns on said detector array, such that said plurality of image replications are formed on different regions of the detector array, readout of said plurality of image replications providing time shift in collection between different replications thereby enhancing collection frame rate of the system.

2. The system of claim 1, further comprising a controller connectable to the collection unit and configured and operable to receive and process said one or more image data piece and determine one or more parameters of the object; the controller being configured to utilize data about operation of the rolling shutter type detector unit and extract, from each of said one or more image data piece, said plurality of image replications corresponding to collected speckle patterns, and to process the so extracted images to determine correlation between consecutive speckle patterns indicative of said one or more parameters.

3. The system of claim 1, wherein said light splitter is a diffractive optical element.

4. The system of claim 1, wherein said light splitter is configured to split collected light using refractive or reflective properties.

5. The system of claim 1, wherein each of said one or more image data piece generated by the detector array corresponds to a number of image regions collected at different timing, thereby increasing sampling rate of the system by a factor on the range between 4 and 20.

6. The system of claim 1, wherein said lens arrangement is configured to provide defocused image of the inspection region on the detector array to thereby increase contract of the collected speckle patterns.

7. The system of claim 1, wherein said at least one light splitter is located along an optical path between said lens arrangement and the detector array.

8. The system of claim 1, wherein said rolling shutter type detector unit comprises a digital detector array configured for row-by-row digital readout operation.

9. The system of claim 1, wherein said rolling shutter type detector unit comprises a digital detector array configured for simultaneous readout and a moving slit providing rolling shutter exposure operation.

10. The system of claim 1, wherein said collection unit is configured to generate said one or more image data pieces with the collection frame rate that exceeds a frame rate of the detector array by a factor of a number of the replications.

11. A detection unit comprising an optical arrangement and a detector array operable as a rolling shutter detector having certain frame rate, said optical arrangement being configured to collect and image a light pattern arriving from a scene on the detector array, wherein the optical arrangement comprises one or more light splitters configured to generate simultaneously a plurality of image replications of said light pattern being collected from the scene, and project said plurality of image replications on different regions of the detector array, thereby enabling said detection unit to collect image data of the scene at sampling rate that exceeds said certain frame rate of the detector array by a factor of a number of the replications.

* * * * *